United States Patent [19]

Essig et al.

[11] Patent Number: 5,395,391
[45] Date of Patent: Mar. 7, 1995

[54] METHOD FOR CLOSING RESSECTED UTERINE TISSUES

[76] Inventors: Mitchell N. Essig, 227 High Brook Ct., Pelham, N.Y. 10803; Peter J. Wilk, 185 W. End Ave., New York, N.Y. 10023

[21] Appl. No.: 73,349

[22] Filed: Jun. 7, 1993

[51] Int. Cl.⁶ .............................................. A61B 17/04
[52] U.S. Cl. .................... 606/220; 606/139; 606/213
[58] Field of Search .............. 606/213, 216–221, 606/119, 139, 144

[56] References Cited

U.S. PATENT DOCUMENTS

| | | | |
|---|---|---|---|
| 3,166,072 | 1/1965 | Sullivan, Jr. | 606/221 |
| 4,060,089 | 11/1977 | Noiles | 606/220 |
| 4,532,926 | 8/1985 | O'Holla | 606/220 |
| 4,534,350 | 8/1985 | Golden et al. | 606/220 |
| 4,573,469 | 3/1986 | Golden et al. | 606/220 |
| 4,644,953 | 2/1987 | Lahodny et al. | 606/119 |
| 4,724,839 | 2/1988 | Bedi et al. | 606/220 |
| 4,890,613 | 1/1990 | Golden et al. | 606/220 |
| 4,932,960 | 6/1990 | Green et al. | 606/220 |
| 5,059,206 | 10/1991 | Winters | 606/220 |

FOREIGN PATENT DOCUMENTS 3709706 10/1987 Germany ................... 128/6

Primary Examiner—Ralph A. Lewis
Attorney, Agent, or Firm—R. Neil Sudol; Henry D. Coleman

[57] ABSTRACT

In a method for closing a ressection in muscular tissues, distal ends of two surgical instruments are juxtaposed to a muscular organ on opposite sides thereof. The organ is compressed between the distal ends of the instruments by moving those distal ends towards one another. Subsequently, a tack is ejected from one instrument through the ressected region of the organ towards the other instrument so that an end of the tack projects beyond the organ. Then, a locking element is positioned on or attached to the projecting end of the tack. The entire operation can be performed laparoscopically, when the ressected organ is the uterus.

19 Claims, 4 Drawing Sheets

METHOD FOR CLOSING RESSECTED UTERINE TISSUES

BACKGROUND OF THE INVENTION

This invention relates to a surgical technique. More particularly, this invention relates to a method for closing ressected muscular tissues. The invention is especially useful in laparoscopic operations to remove a uterine myoma.

The removal of uterine myomas is frequently accomplished laparoscopically. Laparoscopic surgery involves the insufflation of the abdominal cavity with carbon dioxide and the placement of cannulas in the abdominal wall of the patient. Distal end portions of laparoscopic instruments are inserted through the cannulas for performing an operation inside the abdominal cavity by surgeons manipulating the proximal ends of the instruments. Laparoscopic instruments include a fiber-optic laparoscope which enables visual monitoring of abdominal organs, as well as the distal end portions of the operating instruments.

One difficulty in performing a laparoscopic uterine myoma ressection is the closure of the ressected tissues. There is really no method for effectively and quickly closing a ressetion laparoscopically.

OBJECTS OF THE INVENTION

An object of the present invention is to provide a method for closing ressected tissues.

Another object of the present invention is to provide such a method which is particularly adapted to closing ressected muscular tissues and more particularly adapted to closing ressected uterine tissues.

Another, more particular, object of the present invention is to provide is to provide such a method which may be used in a laparoscopic surgical procedure.

A further particular object of the present invention is to provide such a method which is easy to use.

These and other objects of the present invention will be apparent from the drawings and detailed descriptions herein.

SUMMARY OF THE INVENTION

A method for closing a ressection in muscular tissues comprises the steps of (a) juxtaposing a distal end of a first surgical instrument to a muscular organ on one side of a ressected region of the organ, (b) juxtaposing a distal end of a second surgical instrument to the organ on another side of the ressected region opposite the one side, (c) compressing the organ between the distal ends of the first instrument and the second instrument, (d) ejecting a tack from the first instrument through the ressected region of the organ towards the second instrument upon compression of the organ between the first instrument and the second instrument, so that an end of the tack projects beyond the organ, and (e) positioning a locking element on the projecting end of the tack.

According to another feature of the present invention, the method further comprises the step of cutting off a free end portion of the tack upon ejection thereof. Preferably, the cutting off of the tack end portion is performed subsequently to the positioning of the locking element.

The locking element may take the form of a clip which is attached to the projecting end of the tack. Alternatively, the locking element may be a part of the tack which is shifted or deformed to prevent withdrawal of the tack back through the ressected tissues.

According to a more specific feature of the present invention, the second instrument includes a separable distal end element, while the step of ejecting includes the step of inserting a free end portion of the tack through the distal end element of the second instrument. In that event, the distal end element of the second instrument is separated from the rest of the instrument upon insertion of the free end portion of the tack through the distal end element.

In accordance with a mode of operation of the present invention, the instruments are laparoscopic instruments, the method further comprising the steps of inserting the distal end portions of the instruments into a peritoneal or abdominal cavity through respective trocar sleeves which traverse an abdominal wall. This mode of operation is preferred where the ressected organ is the uterus.

A surgical method for use in operating on a muscular organ comprises, in accordance with another conceptualization of the present invention, the steps of (i) ressecting a region of a muscular organ, (ii) compressing a portion of the organ to close the ressected region thereof, (iii) inserting a surgical tack through the portion of the organ, and (iv) attaching a locking element to an end of the tack projecting from the organ.

Where the tack is inserted from one side of the organ to another side thereof, the step of compressing may include the steps of (1) juxtaposing a distal end of a first surgical instrument to the organ on one side of the ressected region of the organ, (2) juxtaposing a distal end of a second surgical instrument to the organ on another side of the ressected region opposite the one side, and (3) moving the first instrument and the second instrument towards one another.

A method in accordance with the present invention for closing ressected tissues is particularly well adapted to closing ressected muscular tissues and more particularly adapted to closing ressected uterine tissues during laparoscopic operations. The method is straightforward and easy to use.

DETAILED DESCRIPTION

Figure 1A:
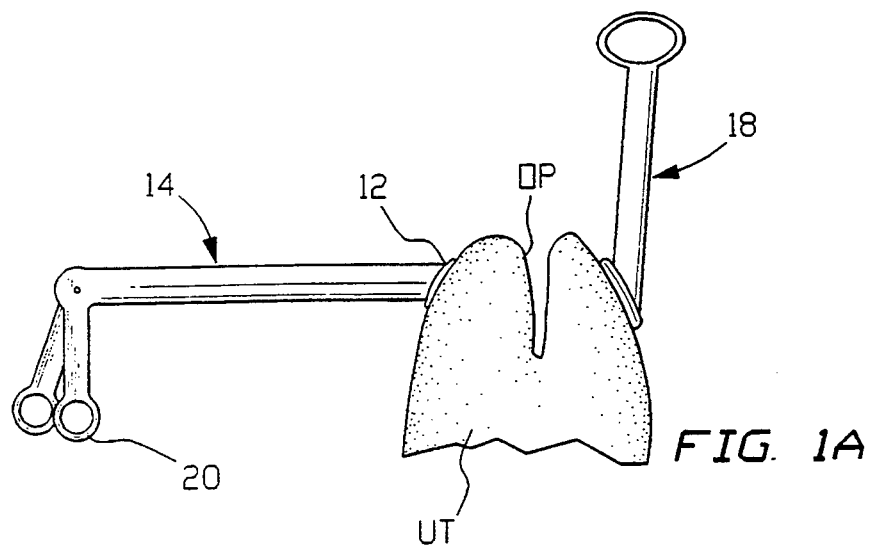
FIGS. 1A through 1E are schematic side elevational views of a uterus and surgical tacking instruments, showing successive stages in a procedure for closing ressected muscle tissues, in accordance with the present invention.
Figure 1B:
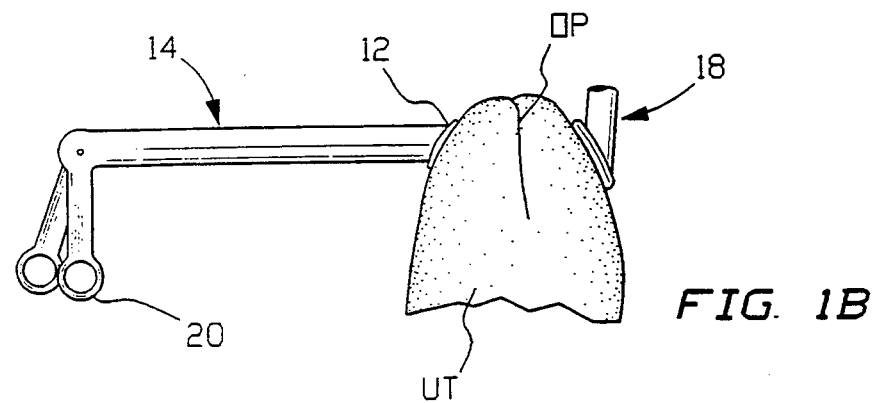
Figure 1C:
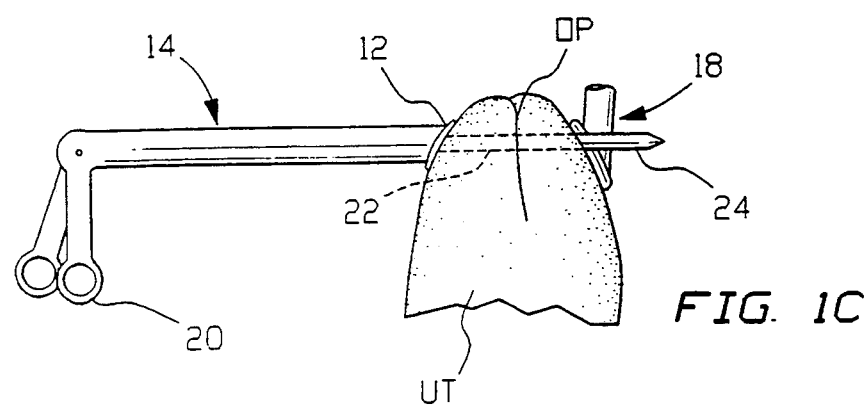

As illustrated in FIG. 1A, to close an opening OP in a uterus UT after ressection thereof, a distal end flange 12 of a tacking ejecting instrument 14 is juxtaposed to the uterus UT on one side of the ressected region. A distal end 16 of a second surgical instrument 18 is juxtaposed to uterus UT on an opposite side of the ressected region. The distal ends 12 and 16 of instruments 14 and 18 are moved towards one another to compress uterus UT between the distal instrument ends and concomitantly to close opening OP, as illustrated in FIG. 1B. An actuator 20 at the proximal end of ejecting instrument 14 is then operated to eject a tack 22 from the distal end of the instrument through the ressected tissues of uterus UT towards instrument 18. Tack 22 is sufficiently long so that a free end 24 of the tack projects beyond uterus UT, as depicted in FIG. 1C.

Figure 1D:
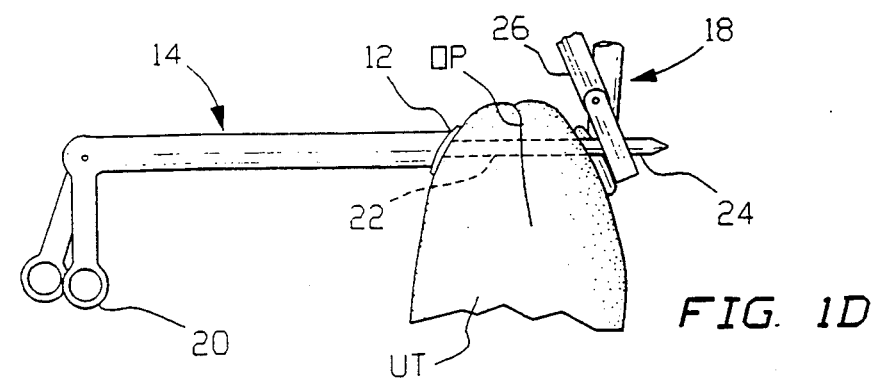

FIG. 1D shows one method of positioning a locking element on tack 22 at the projecting end 24 thereof. A forceps type instrument 26 is used to apply a clip 28 (FIG. 1E) to the projecting end 24 of tack 22. During this procedure, uterus UT remains in a compressed condition, provided that instruments 14 and 18 are maintained in position. As discussed hereinafter with reference to FIG. 12, instruments 14 and 16 may be removed after the ejection of tack 22 and prior to the application of clip 28 if tack 22 is provided with barbs for preventing the movement of the uterine tissues relative to the tack.

Figure 1E:
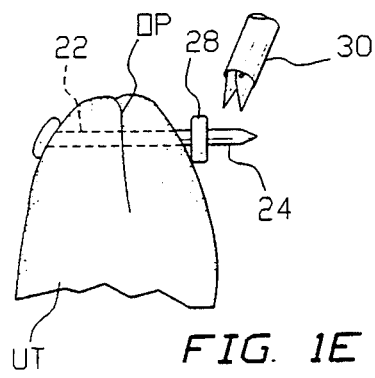

As indicated in FIG. 1E, projecting end portion 24 of tack 22 is severed off by a cutting instrument 30 upon the application of clip 28. It is necessary to cut off the sharp projecting end 24 of tack 22 to avoid damage to other organs of the patient upon completion of the closure operation.

Figure 2:
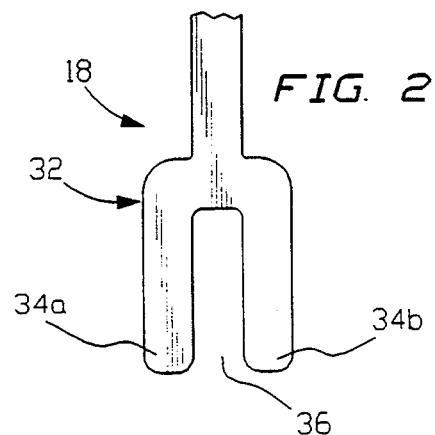
FIG. 2 is an elevational view of a distal end of an instrument for use in a tacking procedure in accordance with the present invention.

As illustrated in FIG. 2, a distal end 32 of surgical instrument 18 may take the form of a pair of flat prongs 34a and 34b extending parallel to one another to define a gap 36 for the passage of the distal end portion 24 of tack 22 during the closure procedure illustrated in FIGS. 1A–1E. Upon the fastening of clip 28 to tack 22, instrument 18 is merely withdrawn in the proximal direction to slide tack 22 out from gap 36.

Figure 3:
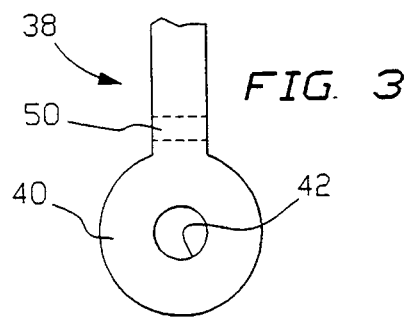
FIG. 3 is an elevational view of a distal end of another instrument for use in a tacking procedure in accordance with the present invention.
Figure 4:
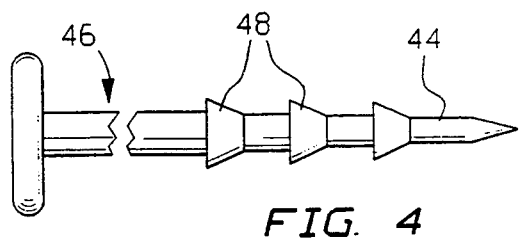
FIG. 4 is a side elevational view of a tack used in a surgical closure procedure with the instrument of FIG. 3.

As illustrated in FIG. 3, a distal end of another surgical clamping instrument 38 for use in place of instrument 18 and clip 28 of FIGS. 1A–1E takes the form of a ring 40 defining an aperture 42 for the passage of a distal end portion 44 of a tack 46 (FIG. 4). Tack 46 is provided along distal end portion 44 with a plurality of conically tapering resilient flanges or projections 48 which serve to lock tack 46 to ring 40 upon insertion of distal end portion 44 through aperture 42. Instrument 38 may be used as a clamping member, in the place of instrument 18 in the procedure of FIGS. 1A–1E. Alternatively, instrument 38 may be used in addition to instrument 18 to attach ring 40 as a locking element to the free end portion of tack 46. In any event, upon a relative movement between ring 40 and tack 46 to insert tack end portion 44 through aperture 42, instrument 38 is severed in a region 50 proximate to ring 40 to separate ring 40 and lock tack 46 to the subject muscle (uterine) tissues.

Figure 5:
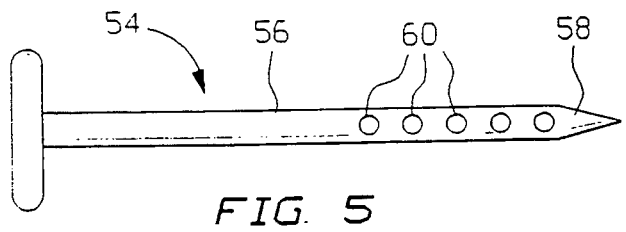
FIG. 5 is a side elevational view of another tack used in a surgical closure procedure in accordance with the present invention.
Figure 6:
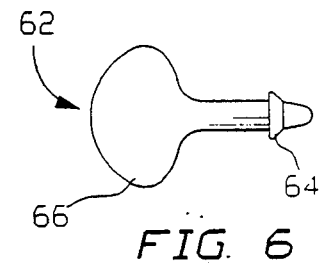
FIG. 6 is a side elevational view of a locking element used with the tack of FIG. 5 to close ressected tissues.

As illustrated in FIG. 5, another tack 54 for use in the procedure of FIGS. 1A–1E (or FIG. 7) comprises a shaft 56 provided along a distal end portion 58 with a plurality of longitudinally or axially spaced bores or apertures 60 for the reception of a locking pin 62 illustrated in FIG. 6. Pin 62 is provided at one end with a resilient detent 64, which is insertable through a selected bore 60, and at an opposite end with an enlarged head portion 66 acting as a stop or arrest upon the placement of the pin. It is to be noted that tacks 46 and 54, as well as tack 22, may be provided with barbs or teeth as described hereinafter with reference to FIG. 12.

Figure 7:
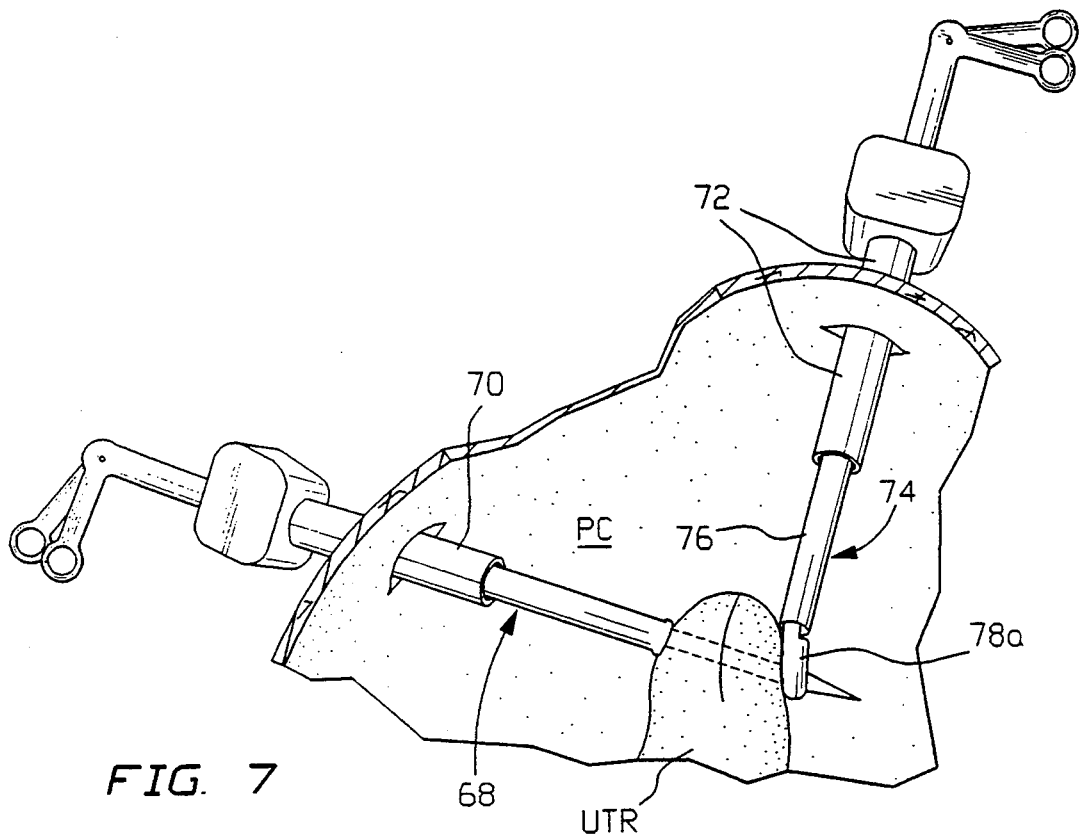
FIG. 7 is a schematic perspective view, partially broken away and partially in cross-section of laparoscopic instrumentation used to close a uterine ressection, in accordance with the present invention.

As depicted in FIG. 7, the technique of FIGS. 1A–1E may be used in a laparoscopic surgical procedure to closure a ressected region RR of a uterus UTR. A distal end portion of an elongate tack ejector 68 is inserted into the abdominal or peritoneal cavity PC of a patient via a first laparoscopic trocar sleeve 70. Sleeve 70, as well as a second trocar sleeve 72, traverses an abdominal wall AW of the patient. A clamping instrument 74 with an elongate shaft 76 is inserted through sleeve 72.

Figure 8:
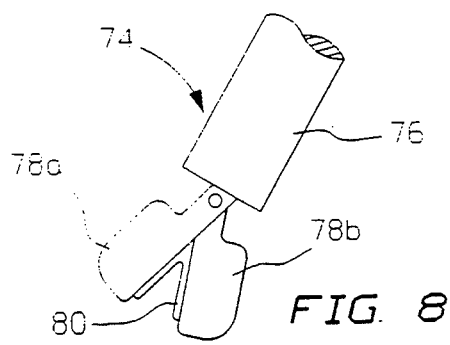
FIG. 8 is a side elevational view of a distal end of an instrument for use in a laparoscopic tacking procedure in accordance with the present invention.
Figure 9:
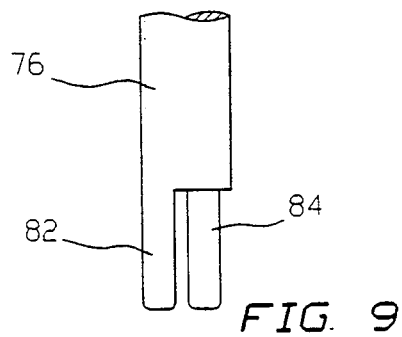
FIG. 9 is a partial elevational view of yet another laparoscopic instrument for use in a uterine closure operation in accordance with the present invention.

As shown in FIG. 8, clamping instrument 74 may be provided at a distal end with flattened forceps jaws 78a and 78b which hold a clip 80. The flattened aspect of jaws 78a and 78b serves to facilitate the pressing of uterus UTR between instruments 68 and 74. FIG. 9 shows a modified version of the instrument wherein an arm 82 extends longitudinally from the distal end of shaft 76. The arm is used to press the uterine tissues against tack ejector 68, while a separate gripping head 84 applies a locking clip.

Figure 10:
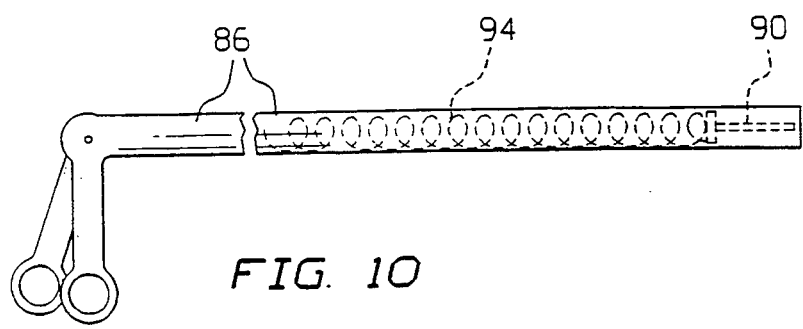
FIG. 10 is a schematic side elevational view, on a reduced scale, of a laparoscopic tacking instrument for use in a surgical procedure in accordance with the present invention.
Figure 11:
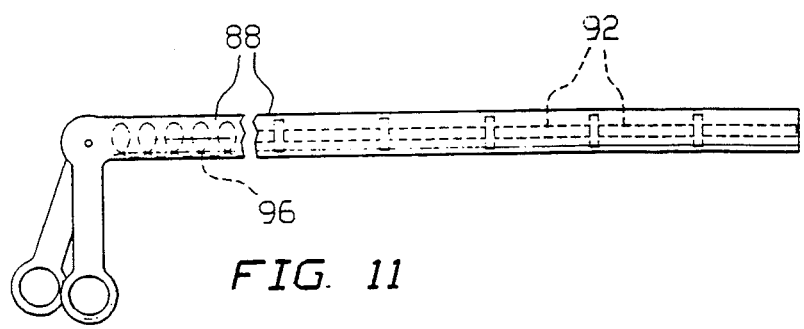
FIG. 11 is a schematic side elevational view, on a reduced scale, of another laparoscopic tacking instrument for use in a surgical procedure in accordance with the present invention.

As shown in FIGS. 10 and 11, laparoscopic tack ejectors 86 and 88 for closing a ressected muscular organ such as a uterus may be provided with a single tack 90 or a plurality of tacks 92 arranged in a magazine. Springs 94 and 96 may provide the driving force for ejecting the tacks.

Figure 12:
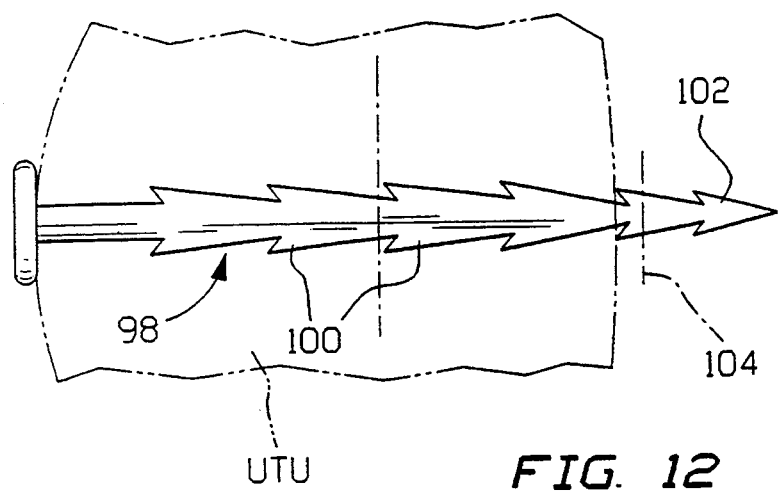
FIG. 12 is a schematic side elevational view, on an enlarged scale, of a tack for closing uterine tissue after ressection, in accordance with the present invention.
Figure 13:
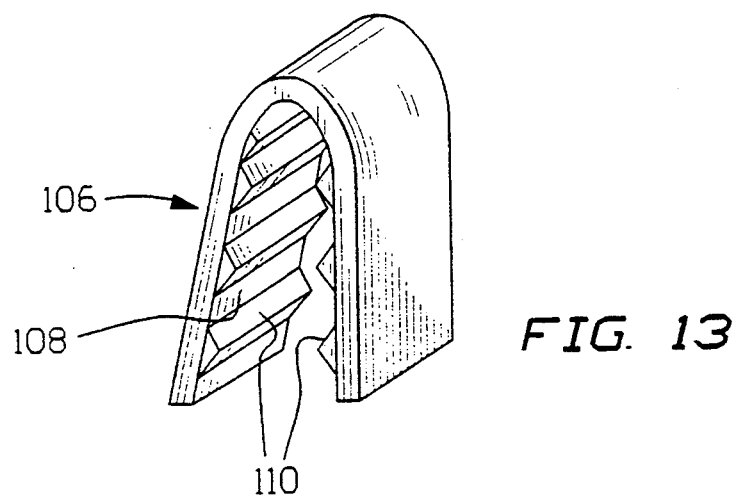

As shown in FIG. 12, a tack 98 closing a ressected muscular organ such as a uterus UTU is provided along a substantial portion of its length with a plurality of barbs or rearwardly oriented teeth 100 which serve to anchor the tack in uterine tissues, i.e., prevent slippage of the uterine tissues relative to the tack. A sharp end portion 102 of tack 98 is severed along a line 104 upon a shooting of the tack through uterine tissues. In addition, a clip 106 as illustrated in FIG. 13 may be connected to tack 98 prior to the severing of end portion 102. Clip 106 is provided along inner surfaces 108 with notches or ridges 110 for enhancing the connection.

Figure 14:
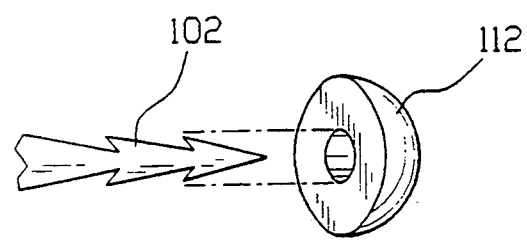

As shown in FIG. 14, a cap 112 instead of a clip 106 may be fastened to the sharp end portion 102 of tack 106 to protect tissues from injury.

It is to be noted that there are other techniques for locking or securing a tack to a muscular organ which are equivalent to the particular embodiments of the invention described herein. For example, a tack may be provided, at an end which is fired through the tissues, with a locking mechanism, such as a pivotable pin or an expandable linkage, as in a molley bolt. The pin or linkage is parallel to the shaft of the tack during insertion thereof through uterine tissues. Upon ejection or the tack, the pin is pivoted to prevent the tack from being withdrawn. A plurality of pins may be provided along a distal end portion of the tack, to enable adjustment of the tack to the thickness of the uterine tissues at the point of ressection.

Any of the tacks described herein may be made of bioabsorbable material.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for closing a ressection in internal muscular tissues, comprising the steps of:
   inserting a distal end portion of a first laparoscopic surgical instrument and a distal end portion of a second laparoscopic surgical instrument into a peritoneal or abdominal cavity of a patient through at least one trocar sleeve which traverses an abdominal wall of the patient;
   juxtaposing the distal end of said first laparoscopic surgical instrument to a muscular organ on one side of a ressected region of the organ;
   juxtaposing the distal end of said second laparoscopic surgical instrument to the organ on another side of said ressected region opposite said one side;
   compressing the organ between the distal ends of said first laparoscopic surgical instrument and said second laparoscopic surgical instrument;
   upon compression of the organ between said first laparoscopic surgical instrument and said second laparoscopic surgical instrument, ejecting a tack from said first laparoscopic surgical instrument through the ressected region of the organ towards said second laparoscopic surgical instrument so that an end of said tack projects beyond the organ; and
   positioning a locking element on the projecting end of said tack.

2. The method defined in claim 1, further comprising the step of cutting off a free end portion of said tack upon completion of said step of ejecting.

3. The method defined in claim 2 wherein said step of cutting is performed subsequently to said step of positioning.

4. The method defined in claim 1 wherein said step of positioning includes the step of securing a locking clip to the projecting end of said tack.

5. The method defined in claim 1 wherein said second laparoscopic surgical instrument includes a separable distal end element, said step of ejecting including the step of inserting a free end portion of said tack through said distal end element of said second laparoscopic surgical instrument, said step of positioning including the step of separating said distal end element of said second laparoscopic surgical instrument upon insertion of said free end portion of said tack through said distal end element.

6. The method defined in claim 1 wherein said first laparoscopic surgical instrument and said second laparoscopic surgical instrument are separate laparoscopic instruments, said step of inserting including the step of inserting the distal end portion of said first laparoscopic surgical instrument and the distal end portion of said second laparoscopic surgical instrument into the peritoneal or abdominal cavity separately through respective trocar sleeves which traverse the abdominal wall.

7. The method defined in claim 1 wherein said organ is the uterus.

8. A surgical method for use in operating on a muscular organ, comprising the steps of:
   ressecting a region of a muscular organ;
   compressing a portion of the organ to close the ressected region thereof, said step of compressing including the steps of:
      juxtaposing a distal end of a first instrument to the organ on one side of said ressected region of the organ;
      juxtaposing a distal end of a second instrument to the organ on another side of said ressected region opposite said one side; and
      moving said first instrument and said second instrument towards one another;
   inserting a surgical tack through said portion of the organ; and
   positioning a locking element on an end of said tack projecting from said organ,
   said first instrument and said second instrument being laparoscopic instruments, further comprising the step of inserting the distal end portion of said first instrument and the distal end portion of said second instrument into a peritoneal or abdominal cavity through respective trocar sleeves which traverse an abdominal wall.

9. The method defined in claim 8 wherein said organ is the uterus.

10. The method defined in claim 8 wherein said step of inserting said surgical tack includes the step of ejecting said tack from said first instrument towards said second instrument upon completion of said step of moving.

11. The method defined in claim 8 wherein said second instrument includes a separable distal end element, said step of ejecting including the step of inserting a free end portion of said tack through said distal end element of said second instrument, also comprising the step of separating said distal end element of said second instrument upon insertion of said free end portion of said tack through said distal end element.

12. The method defined in claim 8 wherein said step of inserting said surgical tack includes the step of ejecting said tack from one of said first instrument and said second instrument.

13. The method defined in claim 8 wherein said tack is inserted from one side of the organ to another side thereof, said step of positioning including the step of securing a clip to an end of said tack on said one side of the organ.

14. The method defined in claim 8 wherein said tack is inserted from one side of the organ to another side thereof, said step of positioning including the step of securing a clip to an end of said tack on said another side of the organ.

15. The method defined in claim 8 wherein a free end portion of said tack projects beyond said locking element, on a side thereof opposite the organ, upon completion of said step of positioning, further comprising the step of cutting off said free end portion upon completion of said step of positioning.

16. A method for closing an opening in internal tissues, comprising the steps of:

inserting a distal end portion of a first laparoscopic surgical instrument and a distal end portion of a second laparoscopic surgical instrument into a peritoneal or abdominal cavity of a patient through at least one trocar sleeve which traverses an abdominal wall of the patient;

juxtaposing the distal end of said first laparoscopic surgical instrument to an internal organ on one side thereof;

juxtaposing the distal end of said second laparoscopic surgical instrument to the organ on another side thereof opposite said one side;

compressing the organ between the distal ends of said first laparoscopic surgical instrument and said second laparoscopic surgical instrument;

upon compression of the organ between said first laparoscopic surgical instrument and said second laparoscopic surgical instrument, ejecting a tack from said first laparoscopic surgical instrument through the organ towards said second laparoscopic surgical instrument so that an end of said tack projects beyond the organ; and positioning a locking element on the projecting end of said tack.

17. The method defined in claim 16, further comprising the step of cutting off a free end portion of said tack upon completion of said step of ejecting.

18. The method defined in claim 16 wherein said second laparoscopic surgical instrument includes a separable distal end element, said step of ejecting including the step of inserting a free end portion of said tack through said distal end element of said second laparoscopic surgical instrument, said step of positioning including the step of separating said distal end element of said second laparoscopic surgical instrument upon insertion of said free end portion of said tack through said distal end element.

19. The method defined in claim 16 wherein said first laparoscopic surgical instrument and said second laparoscopic surgical instrument are separate instruments inserted through respective trocar sleeves into the abdominal or peritoneal cavity.

* * * * *